(12) United States Patent
Kamekawa et al.

(10) Patent No.: US 7,560,593 B2
(45) Date of Patent: Jul. 14, 2009

(54) PROCESS FOR PRODUCING NITROISOUREA DERIVATIVES

(75) Inventors: Hisato Kamekawa, Omuta (JP); Toshiyuki Kohno, Chosei-gun (JP); Hiroyuki Katsuta, Chiba (JP); Daisuke Ura, Omuta (JP); Kenichi Satoh, Ogori (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/278,495

(22) PCT Filed: Feb. 7, 2007

(86) PCT No.: PCT/JP2007/000065
§ 371 (c)(1),
(2), (4) Date: Aug. 6, 2008

(87) PCT Pub. No.: WO2007/091390
PCT Pub. Date: Aug. 16, 2007

(65) Prior Publication Data
US 2009/0018363 A1  Jan. 15, 2009

(30) Foreign Application Priority Data
Feb. 10, 2006  (JP) .............................. 2006-033940

(51) Int. Cl.
*C07C 273/18*  (2006.01)
(52) U.S. Cl. ........................................ 564/108; 564/33
(58) Field of Classification Search .................. 564/33, 564/108
See application file for complete search history.

(56) References Cited

U.S. PATENT DOCUMENTS 6,124,466 A * 9/2000 Matsuno et al. ............. 546/332
6,265,582 B1   7/2001 Uneme et al.

FOREIGN PATENT DOCUMENTS

| JP | 2546003 | B2 | 10/1996 |
| JP | 2766848 | B2 | 6/1998 |
| JP | 2779403 | B2 | 7/1998 |
| JP | 2000-095748 | A | 4/2000 |
| JP | 2000-103775 | A | 4/2000 |
| JP | 2000-103776 | A | 4/2000 |

OTHER PUBLICATIONS

N. Heyboer et al., "Note on the Conversion of the Amino Group of Amino Acids into the Nitroguanidino Group," Recl. Trav. Chim. Pays-Bas, 1962, vol. 81, pp. 69-72.
International Search Report for PCT/JP2007/000065, dated Mar. 30, 2007.

* cited by examiner

*Primary Examiner*—Peter G O'Sullivan
(74) *Attorney, Agent, or Firm*—Buchanan Ingersoll & Rooney PC

(57) ABSTRACT

Disclosed is an improved process for producing nitroisourea derivatives which is necessary for producing nitroguanidine derivatives having an insecticidal activity. Specifically disclosed is a process for producing nitroisourea derivatives represented by the following general formula (3), which is characterized in that nitroisourea derivatives represented by the following general formula (1) and amines represented by the following general formula (2) or a salt thereof are reacted in the presence of a catalytic amount of a hydrogen carbonate,

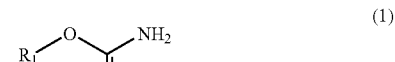
(1)

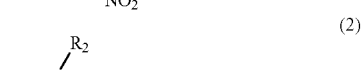

(2)

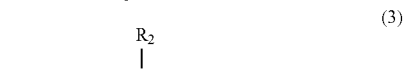

(3)

5 Claims, No Drawings

PROCESS FOR PRODUCING NITROISOUREA DERIVATIVES

TECHNICAL FIELD

The present invention relates to an improved process for producing nitroisourea derivatives that is an important intermediate of nitroguanidine derivatives having an insecticidal activity.

BACKGROUND ART

A process for producing nitroguanidine derivatives having an insecticidal activity has been disclosed in Japanese Patent No. 2779403, Japanese Patent No. 2546003, Japanese Patent No. 2766848. However, for example, as described in Japanese Patent No. 2766848, the problem occurs in the production method that substitution reactions between isothiourea derivatives and amines are used thereby releasing mercaptans as by-products having a strong distasteful odor. As an alternative method, in Japanese Patent Laid-open No. 2000-103776, there has been disclosed a process for producing nitroisourea derivatives in which nitroisourea derivatives and amines or a salt thereof are reacted at the pH of 7.0 to 9.0. However, in a production method according to this method, the desired yield of the nitroisourea derivatives are not sufficiently high and thus the method is economically disadvantageous in some cases.

Patent Document 1: Japanese Patent No. 2779403
Patent Document 2: Japanese Patent No. 2546003
Patent Document 3: Japanese Patent No. 2766848
Patent Document 4: Japanese Patent Laid-open No. 2000-103776

DISCLOSURE OF THE INVENTION

An object of the present invention is to provide a method for cheaply and easily producing nitroisourea derivatives that are intermediates necessary for producing nitroguanidine derivatives having an insecticidal activity, by overcoming the aforementioned problems in the prior art with an easier operation than that used in the prior art.

In order to solve the above objects, the present inventors have conducted an extensive study and as a result, have found that nitroisourea derivatives represented by the general formula (1) and amines represented by the general formula (2) or a salt thereof are reacted in the presence of a hydrogen carbonate, thereby enhancing the yield, and then the present invention has been completed.

That is, the present invention relates to a process for producing nitroisourea derivatives represented by the following general formula (3), in which nitroisourea derivatives represented by the following general formula (1) and amines represented by the following general formula (2) or a salt thereof are reacted in the presence of a catalytic amount of a hydrogen carbonate,

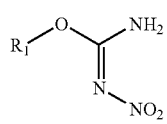
(1)

wherein, in the formula, $R_1$ represents an alkyl group having 1 to 4 carbon atoms or a benzyl group,

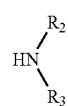
(2)

wherein, in the formula, $R_2$ represents an alkyl group having 1 to 4 carbon atoms; and $R_3$ represents a hydrogen atom or an alkyl group having 1 to 4 carbon atoms,

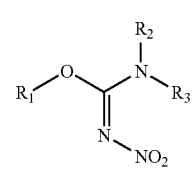
(3)

wherein, in the formula, $R_1$ represents an alkyl group having 1 to 4 carbon atoms or a benzyl group; $R_2$ represents an alkyl group having 1 to 4 carbon atoms; and $R_3$ represents a hydrogen atom or an alkyl group having 1 to 4 carbon atoms.

In addition, in the present invention, the nitroisourea derivatives represented by the general formula (1) may contain nitroisourea derivatives having a double bond between the other nitrogen atom and carbon atom. The nitroisourea derivatives represented by the general formula (3) are the same.

According to the present invention, it is possible to cheaply and easily produce nitroisourea derivatives of the general formula (3) that are essential intermediates for producing nitroguanidine derivatives having an insecticidal activity.

BEST MODE FOR CARRYING OUT THE INVENTION

The present invention will be illustrated in detail below.

The process for producing nitroisourea derivatives of the present invention is a process for producing nitroisourea derivatives represented by the following general formula (3), in which nitroisourea derivatives represented by the following general formula (1) with amines represented by the following general formula (2) or a salt thereof are reacted in the presence of a catalytic amount of a hydrogen carbonate,

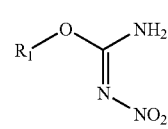
(1)

wherein, in the formula, $R_1$ represents an alkyl group having 1 to 4 carbon atoms or a benzyl group,

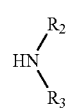
(2)

wherein, in the formula, $R_2$ represents an alkyl group having 1 to 4 carbon atoms; and $R_3$ represents a hydrogen atom or an alkyl group having 1 to 4 carbon atoms,

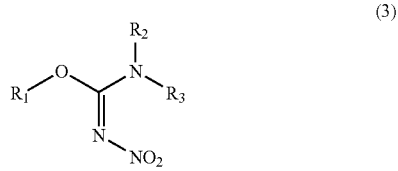

(3)

wherein, in the formula, $R_1$ represents an alkyl group having 1 to 4 carbon atoms or a benzyl group; $R_2$ represents an alkyl group having 1 to 4 carbon atoms; and $R_3$ represents a hydrogen atom or an alkyl group having 1 to 4 carbon atoms.

In the present invention, according to the method in which nitroisourea derivatives represented by the general formula (1) and amines represented by the general formula (2) or a salt thereof are reacted in the presence of a catalytic amount of a hydrogen carbonate, it is possible to suppress the generation of by-products such as nitroguanidine derivatives represented by the following general formula (4) or the like, and it is possible to obtain nitroisourea derivatives represented by the general formula (3) in a high yield,

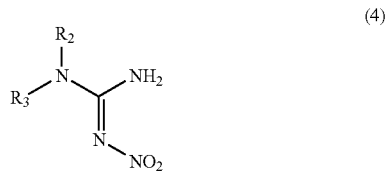

(4)

wherein, in the formula, $R_2$ represents an alkyl group having 1 to 4 carbon atoms; and $R_3$ represents a hydrogen atom or an alkyl group having 1 to 4 carbon atoms.

Examples of the hydrogen carbonate in the present invention include alkali metal hydrogen carbonates such as lithium hydrogen carbonate, sodium hydrogen carbonate, potassium hydrogen carbonate and the like; and alkaline earth metal hydrogen carbonates such as magnesium hydrogen carbonate, calcium hydrogen carbonate, barium hydrogen carbonate and the like. Preferably, potassium hydrogen carbonate and sodium hydrogen carbonate can be used. In the present invention, one or more kinds of these hydrogen carbonates can be used. It is important that the amount of hydrogen carbonate should be a catalytic amount, and specifically from 0.01 to 0.5 mole and preferably from 0.05 to 0.2 mole, based on 1 mole of the foregoing nitroisourea derivatives represented by the general formula (1).

The amount of the hydrogen carbonate within the above range makes it possible to obtain nitroisourea derivatives represented by the general formula (3) in a higher yield.

Examples of the salt of the amines of the general formula (2) include salts of inorganic acids such as hydrochloride, bromate, iodate, sulfate, nitrate, chlorate, perchlorate, phosphate and the like; and salts of organic acids such as acetate, oxalate, benzensulfonate and the like. Hydrochloride and sulfate are preferably used.

The amount of the amines of the general formula (2) or a salt thereof used in the reaction is important because this undergoes a competing reaction with ammonia generated during the reaction. The amine needs to be used more than 2 mole equivalents based on the nitroisourea derivatives represented by the general formula (1). From the economic perspectives, the amount is preferably from more than 2 to not more than 3 mole equivalents.

The nitroisourea derivatives represented by the general formula (1) is a known compound, and can be produced, for example, by a method described in Recl. Trav. Chim. Pays-Bas, Vol. 81, p. 69 (1962) or a method similar thereto.

Examples of the solvent used for the reaction include water; alcohol solvents such as methanol, ethanol, propanol, butanol and the like; halogenated hydrocarbon solvents such as dichloromethane, chloroform and the like; aromatic hydrocarbon solvents such as benzene, toluene, xylene and the like; polar aprotic solvents such as dimethylformamide (DMF), dimethylacetamide, dimethyl sulfoxide, 1,3-dimethyl-2-imidazolidinone, 1-methyl-2-pyrrolidone and the like; ether solvents such as ethyl ether, tetrahydrofuran, dioxane and the like; nitrile solvents such as acetonitrile, propionitrile and the like; and ketone solvents such as acetone, isopropyl ketone and the like. Of these solvents, particularly preferably used are water and alcohols. Furthermore, the reaction can be carried out with a mixed solvent of water and the organic solvent cited before.

When water is selected as a solvent and an aqueous solution containing a neutral inorganic salt is used, it is effective in further enhancing the yield of the nitroisourea derivatives. Such an inorganic salt refers to an inorganic salt other than the hydrogen carbonate, and examples thereof include alkali metal salts such as lithium chloride, sodium chloride, potassium chloride, lithium iodide, sodium iodide, potassium iodide, lithium bromide, sodium bromide, potassium bromide, lithium sulfate, sodium sulfate, potassium sulfate, sodium nitrate, potassium nitrate, sodium chlorate and the like; and alkaline earth metal salts such as magnesium chloride, calcium chloride, magnesium bromide, calcium bromide, magnesium iodide, calcium iodide, magnesium sulfate, calcium sulfate, magnesium nitrate, calcium nitrate and the like. As the inorganic salt, sodium chloride can be preferably used from the viewpoint of the above effect. In the present invention, the inorganic salt can be selected from one or more kinds of these salts and used. The amount of the salt is properly selected in the range of 0.1% concentration to saturation in water, for carrying out the reaction.

In the present invention, by using a hydrogen carbonate, it is possible to suppress the generation of by-products such as the aforementioned nitroguanidine derivatives represented by the general formula (4) or the like. Further, by using an inorganic salt other than the hydrogen carbonate, it is possible to suppress the decomposition of a starting material and a product. For this reason, it is possible to obtain nitroisourea derivatives in a further high yield by a more convenient operation than that used in the prior art. In this way, by the use of a hydrogen carbonate and an inorganic salt other than the hydrogen carbonate, the method can be further excellent in the productivity, environmental sustainability and economical efficiency, and is further useful as an industrial production method.

The reaction temperature is usually in the range of about −20 to 100 degree centigrade and preferably in the range of about 0 to 50 degree centigrade. The reaction time is usually in the range of about 10 minutes to 50 hours and preferably in the range of 1 to 20 hours.

The nitroisourea derivatives of the general formula (3) produced in the present invention can be separated by extraction with a properly selected organic solvent or the like, or it can be separated by filtration as a crystal as it is. Furthermore, when it is separated by filtration as a crystal, the nitroisourea derivatives can be extracted with an organic solvent such as ethyl acetate or the like from the filtrate and used for the reaction again.

EXAMPLES

The present invention is now illustrated in detail below with reference to Examples and Comparative Examples. However, the present invention shall not be limited in any way by these Examples and Comparative Examples.

Example 1

Into a 100-ml, 4-necked flask equipped with a stirrer were introduced 1.5 g of O-methyl-N-nitroisourea, 11 g of water, 3 g of sodium chloride and 2 g of methylamine hydrochloride, and the resulting material was maintained at 20 degree centigrade. Thereafter, 0.1 g of sodium hydrogen carbonate was added to the mixture and the mixture was stirred at 20 degree centigrade for 16 hours. Then, while stirring the reaction mixture, 0.1 g of concentrated hydrochloric acid and 200 ml of water were added to the mixture to give a homogenious aqueous solution of N,O-dimethyl-N'-nitroisourea, which was analyzed by HPLC. In the aqueous solution, 1.2 g of N,O-dimethyl-N'-nitroisourea was contained, and the reaction yield was 73%.

$^1$H-NMR (CDCl$_3$, ppm): 3.02 (3H, d, J=4.9 Hz), 3.97 (3H,), 9.10 (1H, s)

Example 2

Into a 100-ml, 4-necked flask equipped with a stirrer were introduced 1.5 g (11.3 mmole) of O-ethyl-N-nitroisourea, 8 g of water, 2 g of sodium chloride and 2 g (29.6 mmole) of methylamine hydrochloride, and the resulting material was maintained at 15 degree centigrade. Thereafter, 0.1 g of sodium hydrogen carbonate was added to the mixture and the mixture was stirred at 30 degree centigrade for 15 hours. Then, while stirring the reaction mixture, 0.1 g of concentrated hydrochloric acid and 200 ml of water were added to the mixture to give a homogenious aqueous solution of O-ethyl-N-methyl-N'-nitroisourea, which was analyzed by HPLC. In the aqueous solution, 1.2 g of O-ethyl-N-methyl-N'-nitroisourea was contained, and the reaction yield was 70%.

Example 3

Into a 2000-ml, 4-necked flask equipped with a stirrer were introduced 121 g of O-methyl-N-nitroisourea, 907 g of water, 250 g of sodium chloride and 172 g of methylamine hydrochloride, and the resulting material was maintained at 20 degree centigrade. Thereafter, 8 g of sodium hydrogen carbonate was added to the mixture and the mixture was stirred at 20 degree centigrade for 16 hours. Then, while stirring the reaction mixture, 3.5 g of concentrated hydrochloric acid was added to the mixture. After, the reaction mixture was cooled with ice, the precipitated N,O-dimethyl-N'-nitroisourea was collected by filteration, washed with cold water, and then dried. 91 g of an N,O-dimethyl-N'-nitroisourea crystal with a purity of 99% was obtained. The isolated yield was 67%.

Example 4

Into a 2000-ml, 4-necked flask equipped with a stirrer were introduced 97 g of O-methyl-N-nitroisourea, 726 g of water, 200 g of sodium chloride and 138 g of methylamine hydrochloride, and the resulting material was maintained at 20 degree centigrade. Thereafter, 6.4 g of sodium hydrogen carbonate was added to the mixture and the mixture was stirred at 20 degree centigrade for 16 hours. Then, while stirring the reaction mixture, 2.8 g of concentrated hydrochloric acid was added to the mixture. Then, 200 g of ethyl acetate was added to the mixture and the mixture was separated at 50 degree centigrade. Furthermore, the aqueous layer was extracted with 200 g of ethyl acetate two times at 50 degree centigrade, and the combined organic layers were concentrated under a reduced pressure. This concentrated mixture was cooled with ice, and the precipitated N,O-dimethyl-N'-nitroisourea was collected by filteration, washed with cooled ethyl acetate, and then dried. 66 g of an N,O-dimethyl-N'-nitroisourea crystal with a purity of 99% was obtained. The isolated yield was 61%.

Comparative Example 1

To 1.5 g of O-methyl-N-nitroisourea was added 15 ml of water for suspension. 0.9 g of methylamine hydrochloride was added to the aqueous suspension (pH=3.3). An aqueous sodium hydroxide solution (1%) was gradually added to maintain the pH of the aqueous suspension at 8 at room temperature. The aqueous suspension was stirred at room temperature for 3 hours while maintaining the pH thereof at 8, and then an aqueous hydrochloric acid solution (4M) was added to the aqueous suspension and subsequently the aqueous suspension was extracted with ethyl acetate.

In Comparative Example 1, 14 mole % of 1-methyl-2-nitroguanidine was generated as a by-product based on 100 mole % of the starting material. On the other hand, since the reaction proceeded in a high yield and high selectivity by the method described in Example 1, the amount of 1-methyl-2-nitroguanidine of a by-product was 4 mole %, thus greatly reducing the amount of the by-product. That is, according to the present invention, it is possible to reduce the strain during the purification of N,O-dimethyl-N'-nitroisourea. Thus, the method is useful as an industrial production method.

The invention claimed is:
1. A process for producing nitroisourea derivatives represented by the following general formula (3), in which nitroisourea derivatives represented by the following general formula (1) and amines represented by the following general formula (2) or a salt thereof are reacted in the presence of a catalytic amount of a hydrogen carbonate,

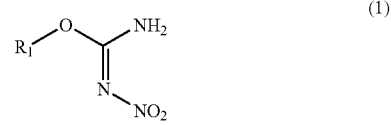

(1)

wherein, in the formula, R$_1$, represents an alkyl group having 1 to 4 carbon atoms or a benzyl group,

(2)

wherein, in the formula, R₂ represents an alkyl group having 1 to 4 carbon atoms; and R₃ represents a hydrogen atom or an alkyl group having 1 to 4 carbon atoms,

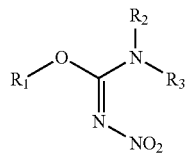
(3)

wherein, in the formula, R₁ represents an alkyl group having 1 to 4 carbon atoms or a benzyl group; R₂ represents an alkyl group having 1 to 4 carbon atoms; and R₃ represents a hydrogen atom or an alkyl group having 1 to 4 carbon atoms.

2. The process for producing nitroisourea derivatives as set forth in claim 1, in which an aqueous solution obtained by dissolving an inorganic salt other than said hydrogen carbonate is used as a solvent.

3. The process for producing nitroisourea derivatives as set forth in claim 2, in which said inorganic salt other than said hydrogen carbonate is sodium chloride.

4. The process for producing nitroisourea derivatives as set forth in claim 1, in which the amines represented by the general formula (2) or a salt thereof is used more than 2 mole equivalents, based on the nitroisourea derivatives represented by the general formula (1).

5. The process for producing nitroisourea derivatives as set forth in claim 1 in which R₁ and R₂ are each a methyl group, and R₃ is a hydrogen atom.

* * * * *